United States Patent
Fukuzawa

(10) Patent No.: US 8,263,945 B2
(45) Date of Patent: Sep. 11, 2012

(54) OPTICAL WAVELENGTH DEMULTIPLEXING DETECTOR FOR FLUORESCENCE ANALYSIS AND FLUORESCENCE DETECTION SYSTEM

(75) Inventor: Takashi Fukuzawa, Tokyo (JP)

(73) Assignee: Nippon Sheet Glass Company, Limited, Tokyo (JP)

( * ) Notice: Subject to any disclaimer, the term of this patent is extended or adjusted under 35 U.S.C. 154(b) by 86 days.

(21) Appl. No.: 12/778,359

(22) Filed: May 12, 2010

(65) Prior Publication Data
US 2010/0294948 A1 Nov. 25, 2010

(30) Foreign Application Priority Data
May 19, 2009 (JP) ................................ 2009-120872

(51) Int. Cl.
*G01N 21/64* (2006.01)
(52) U.S. Cl. .................................................. 250/458.1
(58) Field of Classification Search ................ 250/458.1
See application file for complete search history.

(56) References Cited

U.S. PATENT DOCUMENTS

| | | | |
|---|---|---|---|
| 5,612,818 A * | 3/1997 | Kumagai et al. | 359/385 |
| 7,304,734 B2 | 12/2007 | Fukuzawa et al. | |
| 2003/0122064 A1 * | 7/2003 | Tanaka et al. | 250/227.11 |
| 2005/0100276 A1 * | 5/2005 | Hashizume et al. | 385/34 |
| 2006/0109465 A1 | 5/2006 | Fukuzawa et al. | |
| 2006/0281974 A1 * | 12/2006 | Lei et al. | 600/176 |

FOREIGN PATENT DOCUMENTS

JP 2005-030830 A 2/2005

* cited by examiner

*Primary Examiner* — Kiho Kim
(74) *Attorney, Agent, or Firm* — Holtz, Holtz, Goodman & Chick, PC

(57) ABSTRACT

An optical wavelength demultiplexing detector for fluorescence analysis that is compact, has a small number of components, and is easy to assemble. An excitation light received via a first optical transmission path is outputted to a second optical transmission path, and a fluorescence arising from the excitation light outputted from the second optical transmission path is received via the second optical transmission path and detected. The excitation light having propagated through the first optical transmission path and the fluorescence having propagated through the second optical transmission path are received by the same surface of a first lens. An optical wavelength selection member comprised of a dielectric multilayer film receives the excitation light and the fluorescence passed through the first lens, and reflects the excitation light and passes the fluorescence. A photoelectric conversion element directly receives the fluorescence passed through the first optical wavelength selection member.

10 Claims, 4 Drawing Sheets

OPTICAL WAVELENGTH DEMULTIPLEXING DETECTOR FOR FLUORESCENCE ANALYSIS AND FLUORESCENCE DETECTION SYSTEM

BACKGROUND OF THE INVENTION

1. Field of the Invention

The present invention relates to an optical wavelength demultiplexing detector for fluorescence analysis and a fluorescence detection system having the same.

2. Description of the Related Art

To detect a trace quantity of material being present in a minute region such as a micro-well, a micro-chemical chip, a micro-capillary, or the like, optical measurement methods such as thermal lens spectrophotometry and fluorescence spectrometry are commonly used.

In the fluorescence spectrometry, by irradiating light with a predetermined wavelength onto a sample, and measuring a fluorescence emitted by the sample, a concentration of a material to be measured included in the sample is measured. As a system for such fluorescence detection, a fluorescence detection system with an arrangement shown in FIG. 6 has been proposed (see, for example, Japanese Laid-Open Patent Publication (Kokai) No. 2005-30830).

In this fluorescence detection system, light with a predetermined wavelength (an excitation light) emitted from a light source 91 is transmitted to an optical demultiplexer 92 via an optical fiber 95 (a first optical transmission path), then transmitted from the optical demultiplexer 92 to an optical fiber 96 (a second optical transmission path), and after that, outputted from a probe 94 mounted at a distal end of the optical fiber 96 toward a sample 99. A fluorescence emitted by the sample as a result of the irradiation of the excitation light is received by the probe 94, transmitted to the optical demultiplexer 92 via the optical fiber 96, then transmitted to a detector 93 through an optical fiber 97 (a third optical transmission path), and converted into an electric signal by a detector 93.

FIG. 7 schematically shows an arrangement of the optical demultiplexer used in the fluorescence detection system in FIG. 6. The optical demultiplexer 92 is arranged such that two lenses 82 and 83 disposed with an optical demultiplexing filter 81 interposed therebetween, a first capillary 84 that holds the optical fibers 95 and 96, and is disposed on the lens 82 side, and a second capillary 85 that holds the optical fiber 97 and is disposed on the lens 83 side are held by a cylindrical holding member 86.

The excitation light generated by the light source 91 is outputted from the optical fiber 95 to the lens 82, passes through the lens 82 to be reflected by the optical demultiplexing filter 81, and passes through the lens 82 to fall upon the optical fiber 96. Also, the fluorescence generated by the sample 99 propagates through the optical fiber 96, is outputted to the lens 82, passes through the lens 82 and the optical demultiplexing filter 81 to fall upon the lens 83, passes through the lens 83 to fall upon the optical fiber 97, propagates through the optical fiber 97, and is guided to the detector 93.

However, an optical fiber has a minimum winding radius (bending minimum curvature), and cannot be bent to the value or less, and hence when a number of optical fibers are used, they occupy a wide space in the apparatus. It is thus preferred that the number of optical fibers to be used is minimized. Moreover, because the apparatus must be handled in such a manner as not to break optical fibers, it is preferred that the number of optical fibers to be used is minimized so as to make the apparatus easier to handle. Further, the optical demultiplexer 92 arranged as shown in FIG. 7 has a number of components and takes a lot of time to assemble, and hence its production cost is high.

SUMMARY OF THE INVENTION

The present invention provides an optical wavelength demultiplexing detector for fluorescence analysis that is compact, has a small number of components, and is easy to assemble, and a fluorescence detection system having the optical wavelength demultiplexing detector for fluorescence analysis.

Accordingly, in a first aspect of the present invention, there is provided an optical wavelength demultiplexing detector for fluorescence analysis that outputs an excitation light received via a first optical transmission path to a second optical transmission path, receives via the second optical transmission path a fluorescence arising from the excitation light outputted from the second optical transmission path, and detects the fluorescence, comprising a first lens that receives, on the same surface, the excitation light having propagated through the first optical transmission path and the fluorescence having propagated through the second optical transmission path, a first optical wavelength selection member comprising a dielectric multilayer film that receives the excitation light and the fluorescence passed through the first lens, and reflects the excitation light and passes the fluorescence, and a photoelectric conversion element that directly receives the fluorescence passed through the first optical wavelength selection member.

According to the first aspect of the present invention, because the number of components is small, the apparatus can be made compact. Moreover, due to a reduced number of components, manufacture man-hours for the apparatus are reduced, too, and this can reduce component cost and manufacturing cost, resulting in reduction of product cost. Further, the apparatus becomes easier to assemble. Moreover, because in the optical wavelength demultiplexing detector for fluorescence analysis, a portion that carries out optical demultiplexing and a portion that carries out fluorescence detection are configured as an integral unit, and there is no need to dispose a waveguide such as an optical fiber for optical transmission, the apparatus becomes easier to handle.

The first aspect of the present invention can provide an optical wavelength demultiplexing detector for fluorescence analysis, wherein the first optical transmission path and the second optical transmission path are each an optical fiber and/or an optical waveguide.

According to the first aspect of the present invention, the arrangement of the optical wavelength demultiplexing detector for fluorescence analysis can be simplified, and an optical system can be easily designed.

The first aspect of the present invention can provide an optical wavelength demultiplexing detector for fluorescence analysis, wherein the first optical transmission path and the second optical transmission path are located in the vicinity of the first lens and parallel to an optical axis of the first lens.

According to the first aspect of the present invention, propagation of the excitation light in the optical wavelength demultiplexing detector for fluorescence analysis can be performed with high efficiency using a simple and compact arrangement. Moreover, the excitation light and the fluorescence passed through the optical wavelength selection member can be easily separated.

The first aspect of the present invention can provide an optical wavelength demultiplexing detector for fluorescence"

analysis, further comprising a second lens disposed between the first optical wavelength selection member and the photoelectric conversion element.

According to the first aspect of the present invention, because the fluorescence is collected by the second lens to enter the photoelectric conversion element, the sensitivity for fluorescence detection can be improved. Moreover, because the photoelectric conversion element of which light-receiving area is small can be used, the apparatus can be reduced in size and cost.

The first aspect of the present invention can provide an optical wavelength demultiplexing detector for fluorescence analysis, further comprising a second optical wavelength selection member disposed between the second lens and the photoelectric conversion element.

According to the first aspect of the present invention, a noise light detected due to the excitation light during fluorescence measurement can be efficiently removed, which results in improvement of the sensitivity for fluorescence detection.

The first aspect of the present invention can provide an optical wavelength demultiplexing detector for fluorescence analysis, wherein the second lens and the photoelectric conversion element are disposed such that the fluorescence passed through the second lens is focused on the photoelectric conversion element.

According to the first aspect of the present invention, the sensitivity for fluorescence detection can be further improved.

The first aspect of the present invention can provide an optical wavelength demultiplexing detector for fluorescence analysis, further comprising a light shield member that is disposed on the second lens side of the photoelectric conversion element and has a pinhole.

According to the first aspect of the present invention, a noise light detected due to the excitation light during fluorescence measurement can be efficiently removed, which results in improvement of the sensitivity for fluorescence detection.

The first aspect of the present invention can provide an optical wavelength demultiplexing detector for fluorescence analysis, wherein the second lens and the light shield member are disposed such that the fluorescence is focused at a location of the pinhole.

According to the first aspect of the present invention, because the fluorescence can be efficiently collected, the sensitivity for fluorescence detection can be further improved.

The first aspect of the present invention can provide an optical wavelength demultiplexing detector for fluorescence analysis, further comprising a first cylindrical member that holds the first lens and the first optical wavelength selection member, a holding member that holds the photoelectric conversion element, and a second cylindrical member mounted on the holding member, wherein the first cylindrical member is impacted into the second cylindrical member.

According to the first aspect of the present invention, optical axes of component parts can be easily aligned. As result, an optical system in which the sensitivity for fluorescence detection by the photoelectric conversion element is improved to the greatest extent possible can be easily realized.

Accordingly, in a second aspect of the present invention, there is provided a fluorescence detection system comprising an optical wavelength demultiplexing detector for fluorescence analysis, an excitation light source that outputs the excitation light, the first optical transmission path that connects the excitation light source and the optical wavelength demultiplexing detector for fluorescence analysis together, a probe that irradiates the excitation light onto a sample and receives the fluorescence generated from the sample, and the second optical transmission path that connects the probe and the optical wavelength demultiplexing detector for fluorescence analysis together.

The features and advantages of the invention will become more apparent from the following detailed description in conjunction with the accompanying drawings.

DESCRIPTION OF THE EMBODIMENTS

The present invention will now be described in detail with reference to the drawings showing embodiments thereof.

Figure 1:
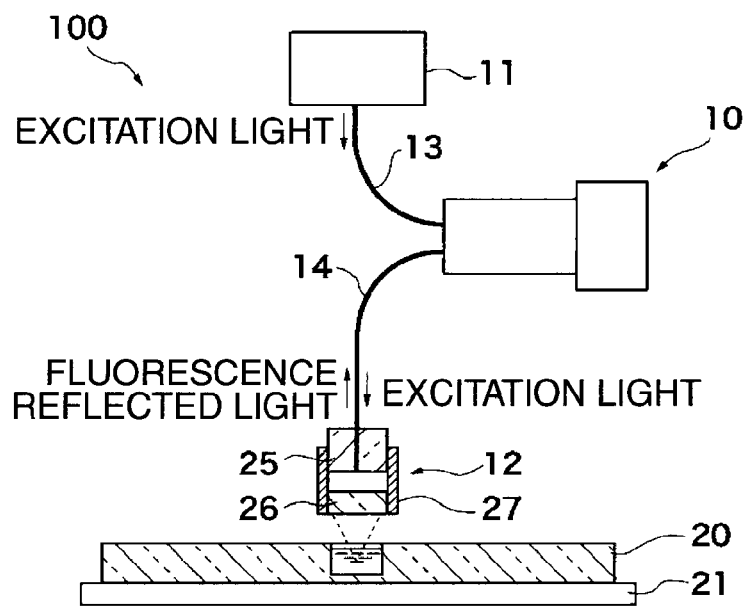
FIG. 1 is a diagram schematically showing an arrangement of a fluorescence detection system having an optical wavelength demultiplexing detector for fluorescence analysis according to a first embodiment of the present invention.

FIG. 1 is a diagram schematically showing an arrangement of a fluorescence detection system having an optical wavelength demultiplexing detector for fluorescence analysis (hereinafter referred to as "the optical wavelength demultiplexing detector") according to a first embodiment of the present invention.

The fluorescence detection system 100 has the optical wavelength demultiplexing detector 10, an excitation light source 11, a probe 12, an optical fiber 13 as a first optical transmission path that connects the optical wavelength demultiplexing detector 10 and the excitation light source 11 together, and an optical fiber 14 as a second optical transmission path that connects the optical wavelength demultiplexing detector 10 and the probe 12 together.

The excitation light source 11 outputs an excitation light that is to be irradiated onto a fluorescence analytical chip 20 to be measured, and for example, an LED (light-emitting diode) or an LD (semiconductor laser diode) that emits light with a dominant wavelength $\lambda_1$ of 470 nm is used as the excitation light source 11. The excitation light outputted from the excitation light source 11 falls upon a lens (not shown) via a short-wavelength transmissive filter (not shown) that passes light with wavelengths not greater than 480 nm, and is focused by the lens to fall upon the optical fiber 13. Then, the excitation light propagates through the optical fiber 13, and is guided to the optical wavelength demultiplexing detector 10. As the optical fiber 13, an optical fiber made of quarts or quarts glass is used so as to enable the excitation light with the dominant wavelength $\lambda_1$ of 470 nm to propagate with low loss.

A detailed description will be given later of an arrangement of the optical wavelength demultiplexing detector 10. The excitation light having propagated through the optical fiber 13 is guided in the optical wavelength demultiplexing detector 10 to the optical fiber 14, and propagates through the optical fiber 14 and is guided to the probe 12. Then, the excitation light is outputted from the probe 12 and irradiated on the fluorescence analytical chip 20 mounted on a stage 21. As is the case with the optical fiber 13, an optical fiber made of quarts or quarts glass is used as the optical fiber 14.

The probe 12 is comprised of a ferrule 25 that holds a distal end of the optical fiber 14, a lens 26 that is optically connected to the optical fiber 14, and a cylindrical fixing member 27 that fixes the ferrule 25 and the lens 26, and is adapted to have, for example, a one-to-one combination system in which a 100% magnification image is formed on an end face of the optical fiber 14. Optical axes of the optical fiber 14 and the lens 26 are aligned with high accuracy, and the excitation light is outputted from the lens 26.

A reflected light of the excitation light irradiated from the probe 12 (hereinafter referred to merely as "the reflected light") and a fluorescence emitted by the fluorescence analytical chip 20 due to the irradiation of the excitation light are collected by the lens 26 to fall upon the optical fiber 14, and propagates through the optical fiber 14 and is guided the optical wavelength demultiplexing detector 10. In the optical wavelength demultiplexing detector 10, the fluorescence is converted into an electric signal, and on the other hand, part of the reflected light is converted into an electric signal (which will be a "base signal", described later), and the remainder returns mainly to the optical fiber 13.

The stage 21 has a moving mechanism (not shown) that moves relatively to the probe 12 and positions the fluorescence analytical chip 20. It should be noted that the probe 12 may be adapted to move relatively to the stage 21.

In the fluorescence detection system 100, although the optical fibers 13 and 14 are used for the propagation of the excitation light and the fluorescence, optical waveguides may be used in place of the optical fibers 13 and 14.

Figure 2:
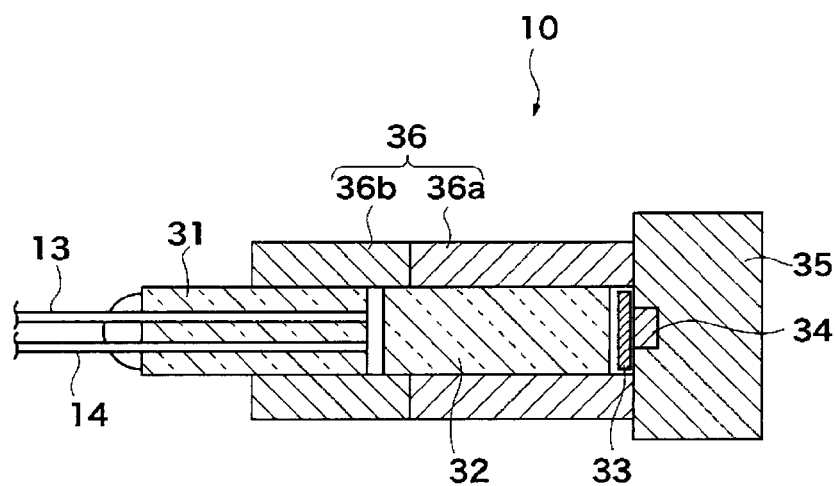
FIG. 2 is a cross-sectional view schematically showing the optical wavelength demultiplexing detector for fluorescence analysis according to the first embodiment of the present invention.

A detailed description will now be given of an arrangement of the optical wavelength demultiplexing detector 10. FIG. 2 is a cross-sectional view showing the arrangement of the optical wavelength demultiplexing detector.

The optical wavelength demultiplexing detector 10 has a capillary 31 that holds the optical fibers 13 and 14, a lens 32 that is optically connected to the optical fibers 13 and 14, an optical wavelength selection member 33 that wavelength-separates light outputted from the lens 32, a photoelectric conversion element 34 that receives light passed through the optical wavelength selection member 33 (light passed through the optical wavelength selection member 33 among the fluorescence, the excitation light, and the reflected light), a holding member 35 that holds the photoelectric conversion element 34, and a cylindrical member 36 that holds the capillary 31 and the lens 32.

As the capillary 31, for example, one made of glass such as commercially available borosilicate glass can be used. Holes of the capillary 31 which hold the optical fibers 13 and 14 are located parallel to the longitudinal direction of the capillary 31 in the light of properties of the lens 32, described below, and therefore, the optical axes can be easily aligned.

In the optical wavelength demultiplexing detector 10, the capillary 31 holds the optical fibers 13 and 14 parallel to each other, and hence the excitation light having propagated through the optical fiber 13 and the fluorescence having propagated through the optical fiber 14 fall upon the lens 32 from the same surface of the lens 32. Thus, in order to guide the excitation light from the optical fiber 13 to the optical fiber 14 and separate the excitation light and the fluorescence from each other, a gradient index cylindrical rod lens that has a refractive index gradient so that the refractive index can lower from the center of the lens toward outside is used as the lens 32.

The gradient index cylindrical rod lens can be easily manufactured (machined) because both end faces of an entrance plane and an exit plane can be flat planes perpendicular to the direction of the optical axis. Moreover, the gradient index cylindrical rod lens can be easily retracted in the cylindrical member 36, and thus can be easily held (assembled). By making the outer diameter of the lens 32 and the outer diameter of the capillary 31 equal to each other as shown in FIG. 2, both the capillary 31 and the lens 32 can be housed in the cylindrical member 36, and the optical wavelength demultiplexing detector 10 can be easily assembled.

As described above, in the capillary 31, both the optical fibers 13 and 14 are disposed parallel to the longitudinal direction of the capillary 31. For this reason, when both the capillary 31 and the lens 32 are housed in the cylindrical member 36, the optical fibers 13 and 14 are placed in the vicinity of the lens 32 and parallel to the optical axis of the lens 32. Thus, the optical wavelength demultiplexing detector 10 is adapted to easily align the optical axes of the lens 32 and the optical fibers 13 and 14.

The excitation light that is outputted from the optical fiber 13 and falls upon one end face of the lens 32, that is, the capillary 31 side end face (hereinafter refereed to as "the left end") of the lens 32 goes through the lens 32 in accordance with the refractive index gradient of the lens 32, and goes to a central portion of the other end face of the lens 32, that is, the optical wavelength selection member 33 side end face (hereinafter refereed to as "the right end") of the lens 32. The most part of the excitation light is then reflected by the optical wavelength selection member 33, goes through the lens 32 toward the optical fiber 14 in accordance with the refractive index gradient of the lens 32, and falls upon the optical fiber 14.

At this time, in order that the excitation light reflected by the optical wavelength selection member 33 can be made to efficiently fall upon the optical fiber 14, it is preferred that an optical system is designed so as to enable the excitation light to fall upon the optical wavelength selection member 33 in a manner being parallel thereto.

On the other hand, the reflected light and the fluorescence having propagated from the probe 12 through the optical fiber 14 fall upon the lens 32 from the left end of the lens 32, goes through the lens 32 in accordance with the refractive index of the lens 32 to reach the right end of the lens 32. After that, the fluorescence passes through the optical wavelength selection member 33 and is guided to the photoelectric conversion element 34. The most part of the reflected light is reflected by the optical wavelength selection member 33.

The optical wavelength selection member 33 has the property of reflecting the excitation light and the reflected light and passing the fluorescence in the above described manner. Here, there generally exists a relationship of "$\lambda_1 < \lambda_2$" between the dominant wavelength $\lambda_1$ of the excitation light and a dominant wavelength $\lambda_2$ of the fluorescence, and hence a cutoff wavelength $\lambda$ of the optical wavelength selection member 33 is required to be greater than $\lambda_1$ and smaller than $\lambda_2$. Thus, a so-called long-path filter is used as the optical wavelength selection member 33.

The optical wavelength selection member 33 is specifically a dielectric multilayer film in which low-refractive-index layers comprised of $SiO_2$ and the like and high-refractive-index layers comprised of $TiO_2$, $ZrO_2$, $Ta_2O_5$, and the like are multilayered. Regarding its transmission characteristics, it is preferred that the transmissivity for light with the wavelength $\lambda_1$ is not more than −20 db (about 1%), and the transmissivity for light with the wavelength $\lambda_2$ is not less than −3 db (between 97% and 50%). The transmissivity for light with the wavelength $\lambda_1$ is more preferably not more than −30 db, and still more preferably is not more than −35 db.

The optical wavelength selection member 33 may be disposed by forming the optical wavelength selection member 33 on a glass substrate and fixing the substrate to the lens 32 using a resin adhesive agent or the like, or may be directly formed on the right end face of the lens 32 through sputtering. FIG. 2 shows an example where the glass substrate (not shown) on which the optical wavelength selection member 33 is formed is held by the cylindrical member 36. By designing the optical system such that the excitation light falls upon the normal to the optical wavelength selection member 33 at an angle of ±5°, the excitation light reflected by the optical wavelength selection member 33 can be caused to efficiently fall upon the optical fiber 14.

Thus, by combining the capillary 31 that holds the optical fibers 13 and 14 parallel to each other, the lens 32 as the gradient index cylindrical rod lens, and the optical wavelength selection member 33 together, the optical wavelength demultiplexing detector 10 can be made compact, and the incidence of the reflected light from the optical fiber 13 into the optical fiber 14 and the separation of the reflected light and the fluorescence can be reliably performed.

In the optical wavelength demultiplexing detector 10, the optical wavelength selection member 33 and the photoelectric conversion element 34 are disposed in proximity to each other, and thus the fluorescence passed through the optical wavelength selection member 33 is directly received by the photoelectric conversion element 34. Here, the word "directly" means that there is no involvement of a member such as an optical waveguide, an optical fiber, or the like, which guides light in a predetermined direction while repeating total reflection. A concrete space (distance) between the optical wavelength selection member 33 and the photoelectric conversion element 34 depends on shapes (sizes) of various components constituting the optical wavelength demultiplexing detector 10, and is preferably not more than 1 mm, for example. It should be noted that the optical wavelength selection member 33 and the photoelectric conversion element 34 may be fixed together using a translucent resin adhesive agent.

As the photoelectric conversion element 34, an Si-PD, an Si-APD (Si-Avalanche Photodiode), a photomultiplier, or the like is used, and it is preferred that an Si-PD or an Si-APD is preferably used for miniaturization. An electric signal (electric current) obtained by the photoelectric conversion element 34 is inputted to an amplifier (not shown) via an electric wire (not shown), and converted into a voltage signal by the amplifier. Based on the voltage signal, it is possible to carry out fluorescence detection, that is, qualitative analysis and quantitative analysis of a fluorescence emitting material included in the fluorescence analytical chip 20.

It should be noted that the excitation light and the reflected light passed through the optical wavelength selection member 33 are also received by the photoelectric conversion element 34 and converted into electric signals (hereinafter referred to as "the base signals"). Thus, an electric signal arising from the detected fluorescence is obtained by subtracting the base signals from all the electric signals obtained by the photoelectric conversion element 34. As the base signals, electric signals obtained by irradiating the excitation light onto a pseudo sample that emits no fluorescence can be used. From the standpoint of improving fluorescence detection accuracy, it is preferred that one having the same reflecting conditions as the fluorescence analytical chip 20 is used as the pseudo sample, and the photoelectric conversion element 34 has low sensitivity at the dominant wavelength $\lambda_1$ of the excitation light.

The holding member 35 is made of, for example, a metal such as stainless steel or aluminum. The cylindrical member 36 is made of, for example, a metal such as stainless steel.

The cylindrical member 36 is comprised of a first cylindrical portion 36a that mainly holds the lens 32, and a second cylindrical portion 36b that mainly holds the capillary 31. The first cylindrical portion 36a and the holding member 35 are fixed together using, for example, a resin adhesive agent so as to prevent light passed through the optical wavelength selection member 33 from externally leaking. The first cylindrical portion 36a and the second cylindrical portion 36b may be fixed together using a resin adhesive agent, or one may be a male screw and the other one may be a female screw so that a right cylinder can be formed by engaging them together. The cylindrical member 36 may be comprised of an integral member that is not divided into the first cylindrical portion 36a and the second cylindrical portion 36b.

The lens 32 is housed in the first cylindrical portion 36a such that part of an end thereof in the longitudinal direction projects out from an end face of the first cylindrical portion 36a. On the other hand, the capillary 31 is positioned and housed in the second cylindrical portion 36b so as to house the part of the lens 32 which projects out from the first cylindrical portion 36a.

By fixing the second cylindrical portion 36b to the first cylindrical portion 36a using a resin adhesive agent so that the second cylindrical portion 36b housing the capillary 31 can house the part of the lens 32 which projects out from the first cylindrical portion 36a, the optical wavelength demultiplexing detector 10 can be assembled while easily aligning the positions and optical axes of the optical fibers 13 and 14 (the capillary 31) and the lens 32.

Figure 6:
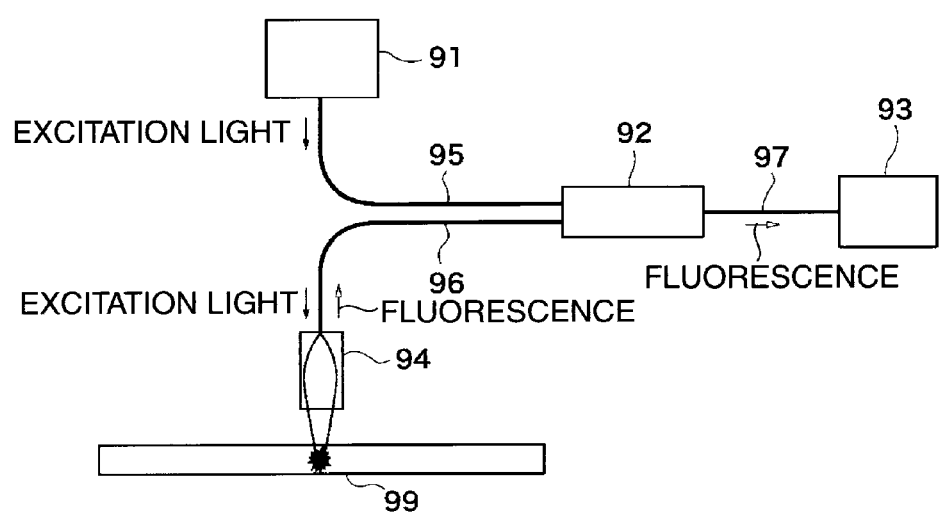
FIG. 6 is a diagram schematically showing an arrangement of a conventional fluorescence detection system.
Figure 7:
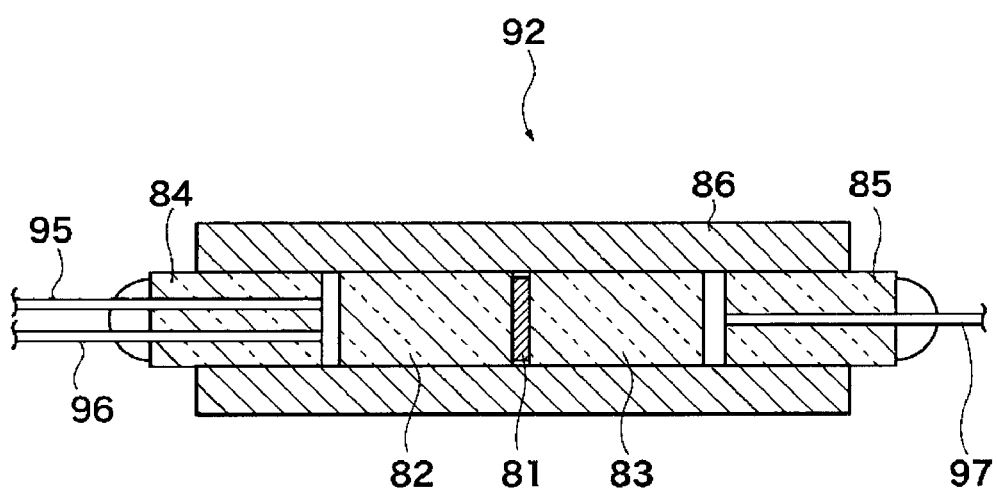
FIG. 7 is a cross-sectional view schematically showing an optical demultiplexer for use in the fluorescence detection system in FIG. 6.

The optical wavelength demultiplexing detector 10 arranged as described above has a smaller number of components as compared with the conventional set of the optical demultiplexer 92 and the detector 93 shown in FIGS. 6 and 7, and thus can be reduced in size and component cost. Moreover, because the number of components is small, the optical wavelength demultiplexing detector 10 can be easily manufactured in reduced production man-hours, and production cost can be reduced. Further, because there is no need to dispose the optical fiber 97 or the like as an optical transmission path between the optical demultiplexer 92 and the detector 93, the apparatus becomes easier to handle.

Figure 3:
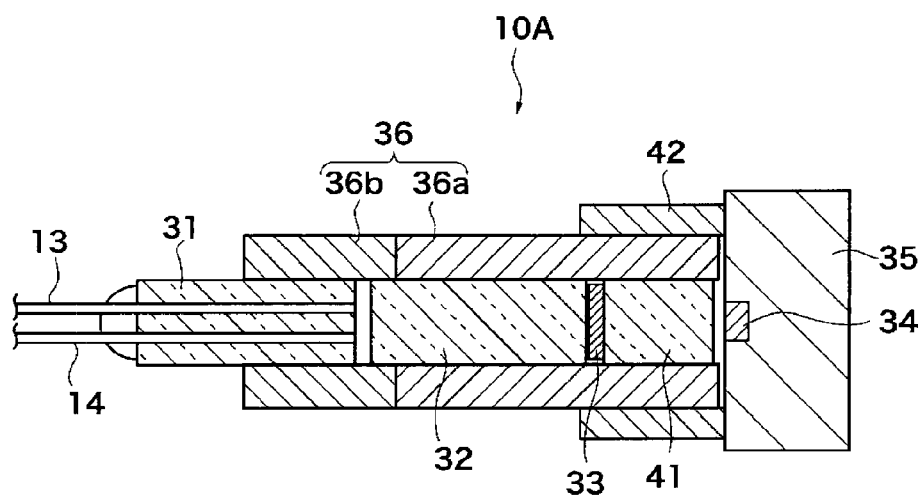
FIG. 3 is a cross-sectional view schematically showing an optical wavelength demultiplexing detector for fluorescence analysis according to a second embodiment of the present invention.

Next, a description will be given of an optical wavelength demultiplexing detector according to a second embodiment of the present invention. FIG. 3 is a cross-sectional view schematically showing the optical wavelength demultiplexing detector according to the second embodiment. Component parts of the optical wavelength demultiplexing detector 10A in FIG. 3 which have the same functions as those of the optical wavelength demultiplexing detector 10 shown in FIG. 2 are denoted by the same reference numerals, and description thereof is omitted.

The optical wavelength demultiplexing detector 10A has the component parts of the optical wavelength demultiplexing detector 10 according to the first embodiment, and additionally has a lens 41 (a second lens) disposed in the cylindrical member 36 such that one end thereof in the longitudinal direction is optically connected to the optical wavelength selection member 33 and the other end thereof in the longitudinal direction faces the photoelectric conversion element 34. It should be noted that in the optical wavelength demultiplexing detector 10A, the optical wavelength selection member 33 is directly formed at a left end of the lens 41.

As is the case with the optical wavelength demultiplexing detector 10 according to the first embodiment, it is preferred that in the optical wavelength demultiplexing detector 10A as well, an excitation light reflected by the optical wavelength selection member 33 is caused to fall upon the normal to the optical wavelength selection member 33 at an angle of ±5° so that the excitation light can fall upon the optical fiber 14 in a more efficient manner. In this case, a fluorescent as well falls upon the normal to the optical wavelength selection member 33 at an angle of ±5°.

In this arrangement, it is preferred that in the optical wavelength demultiplexing detector 10, the photoelectric conversion element 34 of which light-receiving area is wide so as to detect all of the fluorescence passed through the optical wavelength selection member 33, in other words, so as to improve detection sensitivity.

On the other hand, in the optical wavelength demultiplexing detector 10A, a gradient index cylindrical rod lens which is the same as the lens 32 (a first lens) is used as the lens 41 to collect the fluorescence passed through the optical wavelength selection member 33 and irradiate the same upon the photoelectric conversion element 34. As a result, the fluorescence can be efficiently irradiated upon the photoelectric conversion element 34, and detection sensitivity can be improved. Moreover, because the photoelectric conversion element 34 of which light-receiving area is small can be used, component cost in relation to the photoelectric conversion element 34 can be reduced.

The optical wavelength demultiplexing detector 10A is arranged such that a cylindrical member 42 (a second cylindrical member) is fixed to the holding member 35, and the cylindrical member 36 (a first cylindrical member) is inserted and held in the cylindrical member 42. The cylindrical member 42 is fixed to the holding member 35 such that the longitudinal direction thereof is perpendicular to a light-receiving surface of the photoelectric conversion element 34, and its center in the radial direction corresponds to the center of the light-receiving surface of the photoelectric conversion element 34.

The cylindrical members 36 and 42 can be positioned and fixed in, for example, a manner described hereafter. Specifically, with the cylindrical member 36 being inserted into the cylindrical member 42 by a predetermined length, the cylindrical members 36 and 42 are engaged with each other or separated from each other while the photoelectric conversion element 34 is being made to detect the fluorescence, and a position at which the sensitivity for the photoelectric conversion element 34 is maximum, that is, a position at which the light-receiving surface of the photoelectric conversion element 34 is disposed at a focal position of the lens 41 is found. Then, the cylindrical members 36 and 42 are fixed together, for example, using a resin adhesive agent or by means of soldering at a location where a side face of the cylindrical member 36 intersects an exposed end face of the cylindrical member 42.

Thus, because in the optical wavelength demultiplexing detector 10A, the cylindrical members 36 and 42 are adapted to be engaged with each other in such a manner as to be movable relatively to each other, their positions in the direction of an optical axis can be easily adjusted.

It should be noted that, to enable fluorescences with different wavelengths to be measured using one photoelectric conversion element 34 so as to cope with a situation in which fluorescences with different wavelengths according to materials to be measured are generated, it is preferred that in the optical wavelength demultiplexing detector 10A, the cylindrical members 36 and 42 are adapted to be removably engaged with each other (for example, the cylindrical member 36 is friction-held in the cylindrical member 42), and optical demultiplexer portions with different demultiplexing characteristics (the lenses 32 and 41, the optical wavelength selection member 33, and the cylindrical member 36) are used as a need arises.

Next, a description will be given of an optical wavelength demultiplexing detector according to a third embodiment of the present invention.

Figure 4:
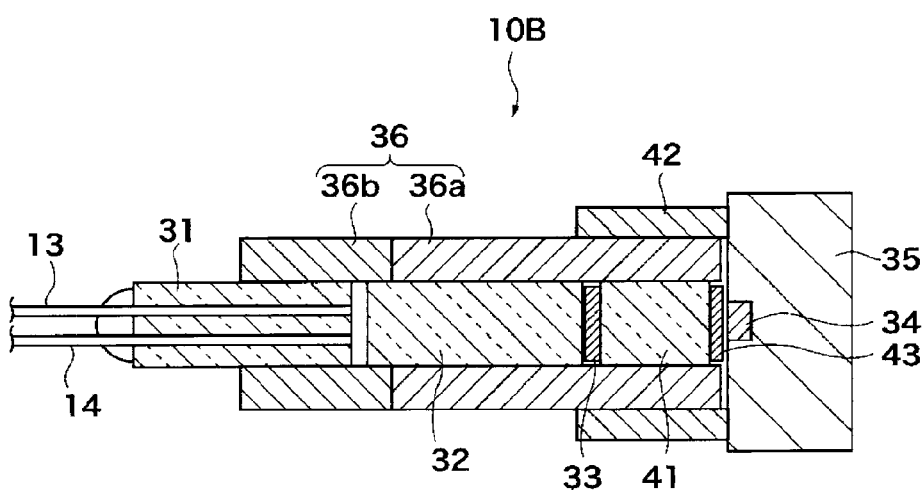
FIG. 4 is a cross-sectional view schematically showing an optical wavelength demultiplexing detector for fluorescence analysis according to a third embodiment of the present invention.

FIG. 4 is a cross-sectional view schematically showing the optical wavelength demultiplexing detector according to the third embodiment. Component parts of the optical wavelength demultiplexing detector 10B in FIG. 4 which have the same functions as those of the optical wavelength demultiplexing detector 10A shown in FIG. 3 are denoted by the same reference numerals, and description thereof is omitted.

The optical wavelength demultiplexing detector 10B has an arrangement in which an optical wavelength selection member 43 (a second optical wavelength selection member) is interposed between the lens 41 and the photoelectric conversion element 34 of the optical wavelength demultiplexing detector 10A according to the second embodiment. The optical wavelength selection member 43 is a filter that cuts an excitation light and a reflected light (an excitation light that will be a base signal) passed through the optical wavelength selection member 33 (a first optical wavelength selection member), and an excitation light and a reflected light (a noise light in fluorescence detection) that has reached the optical wavelength selection member 43 via an outside of (around) the optical wavelength selection member 33.

For example, when a long-path filter that reflects light with wavelengths not more than 490 nm and passes light with wavelengths not less than 500 nm is used as the optical wavelength selection member 33, a long-path filter that reflects light with wavelengths not more than 500 nm and passes light with wavelengths not less than 515 nm can be used as the optical wavelength selection member 43.

By using the optical wavelength selection member 43, light to be detected as base signals during fluorescence detection can be reduced, and also, noise light to be included in base signals can be reduced, resulting in improvement of the sensitivity for fluorescence detection.

Next, a description will be given of an optical wavelength demultiplexing detector according to a fourth embodiment of the present invention.

Figure 5:
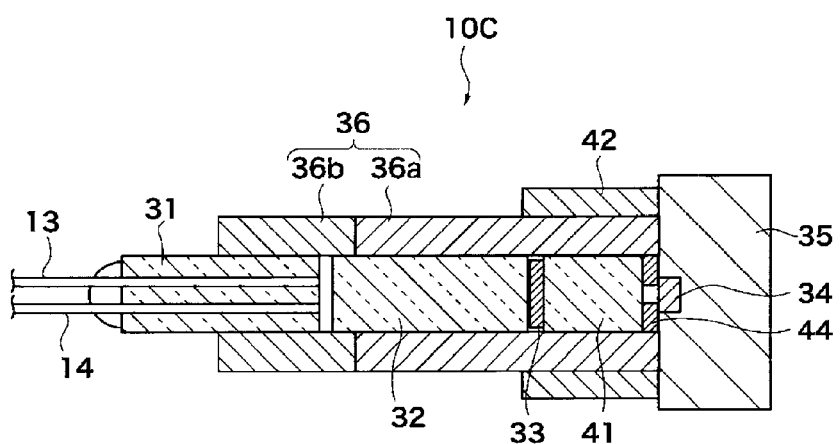
FIG. 5 is a cross-sectional view schematically showing an optical wavelength demultiplexing detector for fluorescence analysis according to a fourth embodiment of the present invention.

FIG. 5 is a cross-sectional view schematically showing the optical wavelength demultiplexing detector according to the fourth embodiment. Component parts of the optical wavelength demultiplexing detector 10C in FIG. 5 which have the same functions as those of the optical wavelength demultiplexing detector 10A shown in FIG. 3 are denoted by the same reference numerals, and description thereof is omitted.

The optical wavelength demultiplexing detector 10C has an arrangement in which a ring-shaped light shield member 44 having a pinhole (hole portion) is interposed between the lens 41 and the photoelectric conversion element 34 of the optical wavelength demultiplexing detector 10A according to the second embodiment.

The light shield member 44 has a function of inhibiting light other than light collected by the lens 41 from entering the photoelectric conversion element 34. Specifically, the light shield member 44 cuts a noise light (an excitation light that has reached the light shield member 44 via an outside of the optical wavelength selection member 33).

The reason why the light shield member 44 has this function is described hereafter. Specifically, depending on a type of a light source used as the excitation light source 11, light with a certain range of wavelengths is included in light outputted from the optical fiber 13. For example, when an LED is used as the excitation light source 11, a slight amount of light with the same wavelength as that of a fluorescence emitted from a material to be measured other than light with a wavelength that can cause the material to be measured to emit the fluorescence is included in an excitation light. The light with the same wavelength as that of the fluorescence passes through the optical wavelength selection member 33. On the other hand, light outputted from the optical fiber 14 includes a reflected light of the excitation light in addition to the fluorescence emitted by the material to be measured.

The focal position of the light outputted from the optical fiber 13 at a right end of the lens 41 (an end face on the photoelectric conversion element 34 side) and the focal position of the light outputted from the optical fiber 14 at the right end of the lens 41 are different in a direction vertical to the optical axis. This is because light exit positions of the optical fibers 13 and 14 are different in the direction vertical to the optical axis, and accordingly, the focal positions as well are different in the direction vertical to the optical axis. Thus, by disposing the light shield member 44 such that the pinhole is located on an optical path of the light outputted from the optical fiber 14, more preferably at the focal position of the fluorescence, the fluorescence outputted from the optical fiber 14 can be passed through the pinhole, and the light outputted from the optical fiber 13 can be cut by the light shield member 44.

It should be noted that through a combined use of the optical wavelength selection member 43 which the optical wavelength demultiplexing detector 10B has and the light shield member 44 which the optical wavelength demultiplexing detector 10C has, a noise light can be cut in a more efficient manner, and the sensitivity for the fluorescence detection can be improved. In this case, it is preferred that the light shield member 44 is disposed on the photoelectric conversion element 34 side. The light shield member 44 mainly cuts a noise light arising from an excitation light outputted from the optical fiber 13, and the optical wavelength selection member 43 mainly cuts a noise light arising from a reflected light included in light outputted from the optical fiber 14.

Next, a description will be given of examples of the present invention, but the present invention is not limited to the examples described hereafter.

«Arrangement of Fluorescence Detection System»

Component elements (parts) of a fabricated fluorescence detection system are listed below. It should be noted that in the excitation light source 11, an excitation light outputted from an LED is guided to the optical fiber 13 via a lens and a filter (passing wavelengths up to 480 nm). The probe 12 is adapted to have a one-to-one combination system in which a 100%-magnification image is formed on an end face of the optical fiber 14.

[Those Related to the Excitation Light Source 11]
  LED: model number=NSPB300B, dominant wavelength $\lambda_1$=470 nm, (manufactured by) Nichia Corporation
  Optical fibers 13 and 14: made of quarts (SI 200/250 (NA=0.22), core diameter=0.2 mm)

[Those Related to the Probe 12]
  Lens 26: model number=SLW18, 0.25 pitch (measured value at a wavelength of 480 nm), (manufactured by) Nippon Sheet Glass Co., Ltd.

[Those Related to the Optical Wavelength Demultiplexing Detector 10]
  Capillary 31: outer diameter=1.8 mmφ, two-axis parallel holes, (manufactured by) Nippon Electric Glass Co., Ltd.
  (First) lens 32: model number=SLW18, 0.25 pitch (measured value at a wavelength of 480 nm), (manufactured by) Nippon Sheet Glass Co., Ltd.
  (First) optical wavelength selection member 33: long-path filter (reflecting region=wavelengths not more than 490 nm, passing region=wavelengths not less than 500 nm)
  Photoelectric conversion element 34: model number=55343, (manufactured by) Hamamatsu Photonics K.K.
  (First) cylindrical member 36: inner diameter=1.8 mmφ, outer diameter=2.5 mmφ, made of SUS

[Those Related to the Optical Wavelength Demultiplexing Detector 10A]
  (Second) lens 41: model number=SLW18, 0.16 pitch (measured value at a wavelength of 480 nm), (manufactured by) Nippon Sheet Glass Co., Ltd.
  (Second) cylindrical member 42: inner diameter=2.5 mmφ, outer diameter=4.0 mmφ, made of SUS

[Those Related to the Optical Wavelength Demultiplexing Detector 10B]
  (Second) optical wavelength selection member 43: long-path filter (reflecting region=wavelengths not more than 500 nm, passing region=wavelengths not less than 515 nm)

[Those Related to the Optical Wavelength Demultiplexing detector 10C]
  Light shield member 44: thickness=0.2 mm, pinhole diameter=0.2 mmφ, outer diameter=1.8 mmφ,

«Sample to be Measured»

An FITC (fluorescein isothiocyanate) aqueous solution (solution concentration: 100 μmol/L (micromole/liter)) was used as a sample that emits a fluorescence. A dominant wavelength $\lambda_2$ of the fluorescence emitted by the FITC is 520 nm.

«Test Results»

Table 1 shows test results. In Table 1, "Example 1" has the same arrangement as that of the optical wavelength demultiplexing detector 10 shown in FIG. 2, "Example 2" has the same arrangement as that of the optical wavelength demultiplexing detector 10A shown in FIG. 3, "Example 3" has the same arrangement as that of the optical wavelength demultiplexing detector 10B shown in FIG. 4, "Example 4" has the same arrangement as that of the optical wavelength demultiplexing detector 10C shown in FIG. 5, and "Example 5" has the component elements of the optical wavelength demultiplexing detector 10A shown in FIG. 3, and additionally has both the optical wavelength selection member 43 and the light shield member 44 that are characteristic component elements of the optical wavelength demultiplexing detectors 10B and 10C shown in FIGS. 4 and 5.

"Base signal" in Table 1 indicates results on measurements conducted on a blank aqueous solution containing no fluorescent material. In Table 1, results of research conducted on variations in base signals by carrying out measurements of base signals (including noise light) with respect to the same blank sample a plurality of times. A signal intensity of fluorescence is found by subtracting a base signal from a measured value (including the fluorescence and the base signal) in a measurement carried out on the sample to be measured.

It was ascertained that a fluorescence can be measured in all the Examples 1 to 5. The sensitivity for fluorescence measurement is greatly affected by a signal-to-noise ratio, and detection sensitivity is higher in an arrangement having a higher signal-to-noise ratio. When Examples 1 to 5 are compared with each other based on this standpoint, the following matter is found.

When Example 1 in which a fluorescences is not collected and the example 2 in which a fluorescence is collected are compared with each other, it is found that in Example 2, not only a fluorescence passed through the optical wavelength selection member 33 but also an excitation light and a reflected light passed through the optical wavelength selection member 33 are collected, and hence a value of a base signal itself tends to be large, and variations also tend to be wide. However, when the amount of the excitation light and the reflected light passed through the optical wavelength selection member 33 is smaller as compared to the amount of the detected fluorescence, the signal-to-noise ratio can be increased by collecting these lights and causing the photoelectric conversion element 34 to collect the same.

When Example 2 and Example 3 are compared with each other, it is found that the signal-to-noise ratio can be increased by the arrangement of Example 3 having (the second) optical wavelength selection member 43 that cuts light resulting in a base signal. Further, it is found that as shown in the result of Example 4, by using the light shield member 44, light resulting in a base signal can be cut in an extremely favorable manner, and the signal-to-noise ratio can be dramatically increased. It is also found that as shown in the result of Example 5, by using the optical wavelength selection member 43 and the light shield member 44 in combination, the signal-to-noise ratio can be further increased.

Thus, according to Examples 1 to 5, it was ascertained that detection sensitivity can be improved by the arrangement in which light resulting in a base signal can be reliably cut while a fluorescence is collected and made to fall upon the photoelectric conversion element 34.

TABLE 1

| Optical wavelength demultiplexing detector | Base signal (*) (signal intensity in case of blank sample) | Standard deviation σ of base signal (base signal variation) | Signal intensity (*) (measured value-base signal) | S/N |
| --- | --- | --- | --- | --- |
| Example 1 | 212 | 1.1 | 11 | 10 |
| Example 2 | 1631 | 2.8 | 118 | 42 |
| Example 3 | 795 | 1.9 | 105 | 55 |
| Example 4 | 9 | 0.2 | 80 | 400 |
| Example 5 | 2 | 0.1 | 68 | 680 |

(*) Unit mV: electric signal (electric current) outputted from photoelectric conversion element is converted into voltage through amplifier and measured

What is claimed is:

1. An optical wavelength demultiplexing detector for fluorescence analysis that outputs an excitation light received via a first optical transmission path to a second optical transmission path, receives via the second optical transmission path a fluorescence arising from the excitation light outputted from the second optical transmission path, and detects the fluorescence, comprising:

a first lens that receives, on the same surface, the excitation light having propagated through the first optical transmission path and the fluorescence having propagated through the second optical transmission path;

a first optical wavelength selection member comprising a dielectric multilayer film that receives the excitation light and the fluorescence passed through said first lens, and reflects the excitation light and passes the fluorescence; and a photoelectric conversion element that directly receives the fluorescence passed through said first optical wavelength selection member.

2. An optical wavelength demultiplexing detector for fluorescence analysis as claimed in claim 1, wherein the first optical transmission path and the second optical transmission path are each an optical fiber and/or an optical waveguide.

3. An optical wavelength demultiplexing detector for fluorescence analysis as claimed in claim 1, wherein the first optical transmission path and the second optical transmission path are located in the vicinity of said first lens and parallel to an optical axis of said first lens.

4. An optical wavelength demultiplexing detector for fluorescence analysis as claimed in claim 1, further comprising a second lens disposed between said first optical wavelength selection member and said photoelectric conversion element.

5. An optical wavelength demultiplexing detector for fluorescence analysis as claimed in claim 4, further comprising a second optical wavelength selection member disposed between said second lens and said photoelectric conversion element.

6. An optical wavelength demultiplexing detector for fluorescence analysis as claimed in claim 4, wherein said second lens and said photoelectric conversion element are disposed such that the fluorescence passed through said second lens is focused on said photoelectric conversion element.

7. An optical wavelength demultiplexing detector for fluorescence analysis as claimed in claim 4, further comprising a light shield member that is disposed on said second lens side of said photoelectric conversion element and has a pinhole.

8. An optical wavelength demultiplexing detector for fluorescence analysis as claimed in claim 7, wherein said second lens and said light shield member are disposed such that the fluorescence is focused at a location of the pinhole.

9. An optical wavelength demultiplexing detector for fluorescence analysis as claimed in claim 1, further comprising:

a first cylindrical member that holds said first lens and said first optical wavelength selection member;

a holding member that holds said photoelectric conversion element; and a second cylindrical member mounted on said holding member, wherein said first cylindrical member is impacted into said second cylindrical member.

10. A fluorescence detection system comprising:
an optical wavelength demultiplexing detector for fluorescence analysis as claimed in claim 1;
an excitation light source that outputs the excitation light;
the first optical transmission path that connects said excitation light source and said optical wavelength demultiplexing detector for fluorescence analysis together;
a probe that irradiates the excitation light onto a sample and receives the fluorescence generated from the sample; and
the second optical transmission path that connects said probe and said optical wavelength demultiplexing detector for fluorescence analysis together.

* * * * *